US007122304B2

(12) United States Patent
Goldsborough et al.

(10) Patent No.: US 7,122,304 B2
(45) Date of Patent: Oct. 17, 2006

(54) METHODS FOR THE STORAGE AND SYNTHESIS OF NUCLEIC ACIDS USING A SOLID SUPPORT

(75) Inventors: Mindy D. Goldsborough, Gaithersburg, MD (US); Donna K. Fox, Sykesville, MD (US)

(73) Assignee: Whatman, Inc., Newton, MA (US)

( * ) Notice: Subject to any disclaimer, the term of this patent is extended or adjusted under 35 U.S.C. 154(b) by 0 days.

(21) Appl. No.: 09/725,897

(22) Filed: Nov. 30, 2000

(65) Prior Publication Data

US 2002/0006615 A1    Jan. 17, 2002

Related U.S. Application Data

(60) Provisional application No. 60/175,307, filed on Jan. 10, 2000.

(51) Int. Cl.
C12Q 1/68    (2006.01)
C12P 19/34   (2006.01)
C12N 1/08    (2006.01)
C07H 21/04   (2006.01)

(52) U.S. Cl. .................. 435/6; 435/91.1; 435/91.51; 435/270; 435/287.2; 536/23.1

(58) Field of Classification Search .............. 435/6, 435/91.1, 183, 287.2, 91.51, 270; 436/501, 436/94; 536/23.1, 23.5, 25.3
See application file for complete search history.

(56) References Cited

U.S. PATENT DOCUMENTS

| 3,416,079 | A |   | 12/1968 | Rey et al.             |
|-----------|---|---|---------|------------------------|
| 4,483,920 | A |   | 11/1984 | Gillespie et al.       |
| 5,496,562 | A |   | 3/1996  | Burgoyne ....... 424/488|
| 5,756,126 | A | * | 5/1998  | Burgoyne ....... 424/488|
| 5,759,820 | A | * | 6/1998  | Hornes et al. .. 435/91.1|
| 5,807,527 | A |   | 9/1998  | Burgoyne               |
| 5,972,386 | A |   | 10/1999 | Burgoyne               |
| 5,976,572 | A | * | 11/1999 | Burgoyne ....... 424/488|
| 5,985,327 | A |   | 11/1999 | Burgoyne               |

FOREIGN PATENT DOCUMENTS

| WO | WO 90/03959 | 4/1990  |
| WO | WO 93/07292 | 4/1993  |
| WO | WO 94/26935 | 11/1994 |
| WO | WO 96/11406 | 4/1996  |
| WO | WO 96/39813 | 12/1996 |
| WO | WO 98/44161 | 10/1998 |
| WO | WO 98/51699 | 11/1998 |

OTHER PUBLICATIONS

Pharmacia Biotech, Biotechnology Products Catalog, 1994, p. 119.*
Pharmacia Biotech Catalog, 1994, p. 119.*
Van Gelder, et al., "Amplified RNA synthesized from limited quantites of heterogeneous cDNA," Proc. Natl. Acad. Sci. USA, vol. 87, pp. 1663-1667, Mar. 1990, Biochemistry.
Copy of International Search Report mailed from the ISA/US Jul. 3, 2001.
Matsubara et al., "Dried blood spot on filter paper as a source of mRNA", Nucleic Acids Research, vol. 20, No. 8, XP-002297049 (1992).
Zhang et al., "RNA analysis from newborn screening dried blood specimens", Human Genetics, 89:311-314 (1992).
Both et al., "FTA Paper, DNA, Time and the Profiler", http://www.bio.flinders.edu.au/vidog.html, (Feb. 22, 1999).
Eisenberg et al., "High throughput automated DNA sample analysis for both RFLP and PCR using FTA <® paper and the Rosys robotic microplate processor", http://www.bio.flinders.edu.au/eisenb.htm, (Feb. 24, 1999).
Perret et al., Improved differential screening approach to analyse transcriptional variations in organized cDNA libraries, Gene, 208:103-115 (1998).
Fellmann et al., Simplified Protocol of Solid-Phase cDNA Libraries for Multiple PCR Amplification, BioTechniques, 21 (5) :766, 768 & 770 (1996).
Lin et al., Detection of Plant Genes Using a Rapid, Nonorganic DNA Purification Method, BioTechniques, 28 (2) :346-350 (2000).
Natarajan et al., Paper-Based Archiving of Mammalian and Plant Samples for RNA Analysis, BioTechniques, 29 (6) :1328-1333 (2000).
Rogers et al., Reverse transcription of an RNA genome from databasing paper (FTA®), Biotechnol. Appl. Biochem., 31:219-224 (2000).
Lambert et al., cDNA library construction from small amounts of RNA using paramagnetic beads and PCR, Nucleic Acids Research, 21 (3) :775-77 (1993).
Seah et al., DNA Databasing on FTA$^R$ paper: Biological Assault and Techniques for Measuring Photogenic Damage, Progress in Forensic Genetics, 8 :74-77 (2000).
"Protocol for the Synthesis of the First Strand of cDNA", Molecular Cloning, A Laboratory Manual, Cold Spring Harbor Laboratory Press, Construction and Analysis of cDNA Libraries, pp. 8.60-8.65 (1989).
Gubler et al., A simple and very efficient method for generating cDNA libraries, Gene, 25:263-269 (1983).
Krug et al., First-Strand cDNA Synthesis Primed with Oligo(dT), Methods in Enzymology, 152:316-325 (1987).

(Continued)

*Primary Examiner*—Bradley L. Sisson
(74) *Attorney, Agent, or Firm*—Edwards Angell Palmer & Dodge, LLP; David G. Conlin; Kathryn A. Piffat

(57) ABSTRACT

The invention relates to storage of nucleic acid (particularly mRNA) on a solid support and to using such nucleic acid in nucleic acid synthesis or amplification reactions. In a preferred aspect, the invention provides synthesis of cDNA and cDNA libraries.

17 Claims, 2 Drawing Sheets

OTHER PUBLICATIONS

Hansen, P. and Blakesley, R., "Simple Archiving of Bacterial and Plasmid DNAs for Future Use", *Focus* 20: 72-74 (1998).

Belgrader, P., Del Rio S.A., Turner, K.A., Marino, M.A., Weaver, K.R., Williams, P.E., "Automated DNA Purification and Amplification from Blood-Stained Cards Using a Robotic Workstation", *BioTechniques*, Short Technical Reports, 19: 426-432 (1995).

*Convenient DNA Collection and Processing: Disposable Toothbrushes and FTA™ Paper as a Non-threaten Buccal-Cell Collection Kit Compatible with Automatable DNA Processing.* Burgoyne, L.A. The Eighth International Symposium on Human Identification: 1997.

Del Rio, S.A., Marino, M., Belgrader. P., "Reusing the same blood-stained punch for sequential DNA amplifications and Typing", *Biotechniques* 20:970-974 (Jun. 1996).

Rogers, C., Burgoyne, L., 1997 "Bacterial Typing: Storing and processing of stabilized reference Bactera for Polymerase Chain Reaction without preparing DNA-An example of an Automatable Procedure", *Analytical Biochemistry* 247, 223-227.

* cited by examiner

METHODS FOR THE STORAGE AND SYNTHESIS OF NUCLEIC ACIDS USING A SOLID SUPPORT

CROSS-REFERENCE TO RELATED APPLICATIONS

The present application claims the benefit of U.S. Provisional Application No. 60/175,307, filed Jan. 10, 2000, the disclosure of which is incorporated herein by reference in its entirety.

BACKGROUND OF THE INVENTION

1. Field of the Invention

The present invention relates to the field of molecular biology. In particular, the present invention relates to the fields of storage, synthesis and amplification of nucleic acids. Specifically the invention relates to storage of RNA (particularly mRNA) on a solid matrix or support and to manipulation of the RNA by a number of molecular biology techniques including RT-PCR and cDNA synthesis (particularly cDNA library synthesis).

2. Related Art

The disclosures of the following applications were incorporated by reference into U.S. Provisional Application No. 60/175,307, filed Jan. 10, 2000, and are incorporated by reference into the present application: U.S. patent application Ser. No. 09/054,485, filed Apr. 3, 1998, now abandoned, which claims priority of U.S. provisional application 60/042,629, filed Apr. 3, 1997, and the continuing application of Ser. No. 09/054,485, U.S. patent application Ser. No. 09/472,066, filed Dec. 23, 1999, now U.S. Pat. No. 6,495,350, issued Dec. 17, 2002; U.S. patent application Ser. No. 09/076,115, filed May 12, 1998, which claims priority of U.S. provisional application 60/046,219, filed May 12, 1997; U.S. patent application Ser. No. 09/354,664, filed Jul. 16, 1999, now U.S. Pat. No. 6,750,059, issued Jun. 15, 2004; and U.S. provisional application Ser. No. 60/122,395, filed Mar. 2, 1999.

Storage of Nucleic Acids

For many projects, generation of numerous DNA samples from biological specimens is routine. Handling and archiving a large collection can become a logistical problem for the laboratory. One solution, used in forensic labs, is the blood-storage medium FTA® Cards. The FTA® GeneCard is a chemically-treated filter paper designed for the collection and storage of biological samples for subsequent DNA analysis (1–3). It is suitable for storage of blood samples, as well as mammalian cells and tissues for PCR analysis and other genomic DNA applications (4). It is useful for recovery of plasmid DNA for PCR and transformation from archived bacterial cultures and colonies (5–6), as well as for storage and recovery of M13 phage for DNA sequencing applications (M. Goldsborough, personal communication).

An FTA® Card can be used to store genomic DNA in the form of dried spots of human whole blood, the cells of which were lysed on the paper. Stored at room temperature, genomic DNA on FTA® paper is reported to be stable at least 7.5 years (Burgoyne, et al., Conventional DNA Collection and Processing: Disposable Toothbrushes and FTA®Paper as a Non-threating Buccal-Cell Collection Kit Compatible with Automatable DNA Processing, 8th International Symposium on Human Identification, Sep. 17–20, 1997). Before analysis of the captured DNA, a few simple washing steps remove the stabilizing chemicals and cellular inhibitors of enzymatic reactions. Since the DNA remains with the paper, the manipulations to purify the DNA are simplified and amenable to automation. DNA samples on FTA® Cards offer a very compact archival system compared to glass vials or plastic tubes located in precious freezer space. Storage of RNA on dry solid medium is also described (see Burgoyne, U.S. Pat. No. 5,976,572).

Reverse Transcription of RNA

The term "reverse transcriptase" describes a class of polymerases characterized as RNA-dependent DNA polymerases. All known reverse transcriptases require a primer to synthesize a DNA transcript from an RNA template. Historically, reverse transcriptase has been used primarily to transcribe mRNA into cDNA which can then be cloned into a vector for further manipulation.

Avian myoblastosis virus (AMV) reverse transcriptase was the first widely used RNA-dependent DNA polymerase (Verma, *Biochem. Biophys. Acta* 473:1(1977)). The enzyme has 5'→3' RNA-directed DNA polymerase activity, 5'→3' DNA-directed DNA polymerase activity, and RNase H activity. RNase H is a processive 5' and 3' ribonuclease specific for the RNA strand for RNA-DNA hybrids (Perbal, *A Practical Guide to Molecular Cloning*, New York: Wiley & Sons (1984)). Errors in transcription cannot be corrected by reverse transcriptase because known viral reverse transcriptases lack the 3'→5' exonuclease activity necessary for proofreading (Saunders and Saunders, *Microbial Genetics Applied to Biotechnology*, London: Croom Helm (1987)). A detailed study of the activity of AMV reverse transcriptase and its associated RNase H activity has been presented by Berger et al., *Biochemistry* 22:2365–2372 (1983).

Another reverse transcriptase which is used extensively in molecular biology is reverse transcriptase originating from Moloney murine leukemia virus (M-MLV). See, e.g., Gerard, G. R., *DNA* 5:271–279 (1986) and Kotewicz, M. L., et al., *Gene* 35:249–258 (1985). M-MLV reverse transcriptase substantially lacking in RNase H activity has also been described. See, e.g., U.S. Pat. No. 5,244,797.

PCR Amplification of RNA

Reverse transcriptases have been extensively used in reverse transcribing RNA prior to PCR amplification. This method, often referred to as RNA-PCR or RT-PCR, is widely used for detection and quantitation of RNA.

To attempt to address the technical problems often associated with RT-PCR, a number of protocols have been developed taking into account the three basic steps of the procedure: (a) the denaturation of RNA and the hybridization of reverse primer; (b) the synthesis of cDNA; and (c) PCR amplification. In the so-called "uncoupled" RT-PCR procedure (e.g., two-step RT-PCR), reverse transcription is performed as an independent step using the optimal buffer condition for reverse transcriptase activity. Following cDNA synthesis, the reaction is diluted to decrease $MgCl_2$ and deoxyribonucleoside triphosphate (dNTP) concentrations to conditions optimal for Taq DNA Polymerase activity, and PCR is carried out according to standard conditions (see U.S. Pat. Nos. 4,683,195 and 4,683,202). In contrast, "coupled" RT-PCR methods use a common or compromised buffer for reverse transcriptase and Taq DNA Polymerase activities. In one version, the annealing of reverse primer is a separate step preceding the addition of enzymes, which are then added to the single reaction vessel. In another version, the reverse transcriptase activity is a component of the thermostable Tth DNA polymerase. Annealing and cDNA synthesis are performed in the presence of Mn++, then PCR is carried out in the presence of Mg++ after the removal of Mn++ by a chelating agent. Finally, the "continuous" method (e.g., one-step RT-PCR) integrates the three RT-PCR steps into a single continuous reaction that avoids the opening of the reaction tube for component or enzyme addition. Continuous RT-PCR has been described as a single enzyme system using the reverse transcriptase activity of thermostable Taq DNA Polymerase and Tth polymerase and as a two-enzyme system using AMVRT and Taq DNA Polymerase wherein the initial 65° C. RNA denaturation step was omitted.

cDNA and cDNA Libraries

In examining the structure and physiology of an organism, tissue or cell, it is often desirable to determine its genetic content. The genetic framework of an organism is encoded in the double-stranded sequence of nucleotide bases in the deoxyribonucleic acid (DNA) which is contained in the somatic and germ cells of the organism. The genetic content of a particular segment of DNA, or gene, is only manifested upon production of the protein which the gene encodes. In order to produce a protein, a complementary copy of one strand of the DNA double helix (the "coding" strand) is produced by polymerase enzymes, resulting in a specific sequence of ribonucleic acid (RNA). This particular type of RNA, since it contains the genetic message from the DNA for production of a protein, is called messenger RNA (mRNA).

Within a given cell, tissue or organism, there exist myriad mRNA species, each encoding a separate and specific protein. This fact provides a powerful tool to investigators interested in studying genetic expression in a tissue or cell—mRNA molecules may be isolated and further manipulated by various molecular biological techniques, thereby allowing the elucidation of the full functional genetic content of a cell, tissue or organism.

One common approach to the study of gene expression is the production of complementary DNA (cDNA) clones. In this technique, the mRNA molecules from an organism are isolated from an extract of the cells or tissues of the organism. This isolation often employs solid chromatography matrices, such as cellulose or Sepharose, to which oligomers of thymidine (T) have been complexed. Since the 3' termini on all eukaryotic mRNA molecules contain a string of adenosine (A) bases, and since A binds to T, the mRNA molecules can be rapidly purified from other molecules and substances in the tissue or cell extract. From these purified mRNA molecules, cDNA copies may be made using an enzyme having reverse transcriptase (RT) activity, which results in the production of single-stranded cDNA molecules complementary to all or a portion of the mRNA templates. Incubating the single-stranded cDNA under appropriate conditions allows synthesis of double-stranded DNA which may then be inserted into a plasmid or a vector.

This entire process, from isolation of mRNA to insertion of the cDNA into a plasmid or vector to growth of host cell populations containing the isolated gene, is termed "cDNA cloning." If cDNAs are prepared from a number of different mRNAs, the resulting set of cDNAs is called a "cDNA library," an appropriate term since the set of cDNAs represents the different populations of functional genetic information (genes) present in the source cell, tissue or organism. Genotypic analysis of these cDNA libraries can yield much information on the structure and function of the organisms from which they were derived.

In traditional production methods, the cDNA molecules must be size fractionated and multiple phenol/chloroform extractions and ethanol precipitations performed. Each of these requirements has inherent disadvantages, such as product loss and limitations in cDNA yield due to multiple extractions/precipitations (Lambert, K. N., and Williamson, V. M., *Nucl. Acids Res.* 21(3):775–776 (1993)).

These disadvantages have been partially addressed in the literature. For example, several investigators have reported methods for the isolation of polyA+ mRNA from cell and tissue samples by binding the mRNA to latex or paramagnetic beads coupled with oligo(dT); single-stranded cDNA molecules may then be produced by reverse transcription of these immobilized mRNA molecules (Lambert, K. N., and Williamson, V. M., *Nucl. Acids Res.* 21(3):775–776 (1993); Kuribayashi-Ohta, K., et al., *Biochim. Biophys. Acta* 1156: 204–212 (1993); Sasaki, Y. F., et al., *Nucl. Acids Res.* 22(6):987–992 (1994); Mészáros, M., and Morton, D. B., *BioTechniques* 20(3):413–419 (1996); Fellman, F., et al., *BioTechniques* 21(5):766–770 (1996)). Such solid phase synthesis methods are less prone to the yield limitations resulting from the extraction/precipitation steps of the traditional methods.

However, these methods still have several important limitations. For example, each of these methods relies on PCR amplification prior to cloning of the cDNA molecules, often resulting in biased cDNA libraries (i.e., highly expressed sequences predominate over those that are expressed in lower quantities). In addition, these methods often are less efficient than conventional cDNA synthesis methods which use solution hybridization of the primer-adapter to the template (i.e., rotational diffusion is required for increased hybridization rates; see Schmitz, K. S., and Schurr, J. M., *J. Phys. Chem.* 76:534–545 (1972); Ness, J. V., and Hahn, W. E., *Nucl. Acids Res.* 10(24):8061–8077 (1982)). Finally, the above-described techniques use heat or chemical denaturation to release the nascent cDNA molecules from the solid phase for further processing, which can result in product loss and/or damage.

BRIEF SUMMARY OF THE INVENTION

The present invention relates to a solid medium or support for use in the storage (preferably the long term storage) of nucleic acids (e.g., DNA and RNA, ribosomal RNA and messenger RNA), particularly polyA RNA or mRNA which comprise the use of this solid medium or support. In particular, the invention relates to a method for storage and transport of such nucleic acids on the solid medium, as well as to methods which involve either recovery of the nucleic acids from the solid medium, and/or the use or manipulation of the nucleic acids obtained from or contained by the solid medium. Such use or manipulation includes, for example, digestion (e.g., with one or more nucleases, exonucleases or endonucleases such as restriction enzymes), synthesis (e.g., with one or more polymerases and/or reverse transcriptases), amplification (e.g., by polymerase chain reaction with one or more polymerases), sequencing (e.g., with one or more polymerases), or transformation or transfection into one or more host cells using, for example, chemically competent or electrocompetent cells or using known transfection reagents and techniques. In a preferred aspect, such manipulation involves RT-PCR, cDNA synthesis or cDNA library construction from RNA obtained from or contained by the solid support. Such manipulations according to the invention can be conducted after storage of the nucleic acids on the support or can be conducted directly without storage. The preferred medium or support is a matrix which protects against degradation of nucleic acids incorporated onto the matrix. Such a matrix may comprise an absorbent cellulose-based matrix or paper, or a micromesh of synthetic plastic material such as those described in U.S. Pat. Nos. 5,496,562 and 5,976,572. Preferably, the matrix comprises a composition comprising a weak base, a chelating agent, an anionic surfactant or anionic detergent, and optionally uric acid or a urate salt, wherein said composition is absorbed on or incorporated into said matrix. FTA® paper (available from Life Technologies, Inc.) and derivatives, variants and modifications thereof are included among such supports. Also included are GenPrep™ and GenSpin™ available from Whatman and IsoCode™ available from Schleicher and Schuell which may also be used according to the invention.

In the practice of the invention, any solid support may be used. Preferred such solid supports include, but are not limited to nitrocellulose, cellulose, diazocellulose, carboxymethylcellulose, hydrophilic polymers (e.g., polyester, polyamide, carbohydrate polymers), polytetra-fluro-ethylene, fiberglass, porous ceramics, polystyrene, polyvinylchloride, polypropylene, polyethylene, dextran, Sepharose, agar, starch, and nylon.

According to the present invention, any nucleic acid molecules (e.g., RNA and DNA and particularly polyA+ RNA and mRNA) may be archived and later recovered and/or manipulated by a simple and efficient method in which a sample (e.g., cells, tissues, cellular materials, etc.) carrying the one or more nucleic acids are contacted with a solid medium (preferably FTA® paper or derivatives, variants or modifications thereof). In another aspect, purified nucleic acid molecules may be used, although in a preferred aspect, crude preparations (unpurified mRNA preparations or cell lysates) containing the one or more nucleic acid molecules may be contacted with the solid medium or support. Thus, any samples may provide the nucleic acid molecules to be contacted or bound to the support such as host cells, viruses, viral plaques, and/or crude preparations from biological materials (such as host cell or virus extracts, lysates, debris, hydrolysates, and the like). Such nucleic acid molecules obtained from or contained by the solid support or matrix may be used or manipulated in one or more standard molecular biology techniques, such as digestion, sequencing, amplification, synthesis and transformation/transfection reactions. Preferably, mRNA obtained from or contained by the solid support is used in RT-PCR or cDNA synthesis and particularly for cDNA library construction. In other preferred embodiments, the RNA obtained according to the invention may be used in Northern blots or attached to other solid supports, such as chips, for use in gene profiling applications. In a particularly preferred aspect, one or more host cells containing the nucleic acid molecules to be isolated, stored and/or manipulated can be contacted directly with the medium or support. According to the present invention, host cell cultures or colonies from plates may be used. Preferred host cells for use in the invention include prokaryotic or eukaryotic host cells, particularly gram positive and gram negative bacteria, plant cells, animal cells (including human), insect cells and the like.

In the practice of the invention, nucleic acid molecules and in particular cDNA molecules or cDNA libraries are produced by mixing one or more nucleic acid templates obtained from or contained by a solid support of the invention (e.g., a mRNA molecule or a polyA+ RNA molecule) with one or more polypeptides having polymerase activity and/or reverse transcriptase activity under conditions favoring synthesis of one or more nucleic acid molecules complementary to all or a portion of the templates.

Preferred polypeptides (e.g., enzymes) having reverse transcriptase and/or polymerase activity to be used in the present invention include, but are not limited to, Moloney Murine Leukemia Virus (M-MLV) reverse transcriptase, Rous Sarcoma Virus (RSV) reverse transcriptase, Avian Myeloblastosis Virus (AMV) reverse transcriptase, Rous Associated Virus (RAV) reverse transcriptase, Myeloblastosis Associated Virus (MAV) reverse transcriptase, Human Immunodeficiency Virus (HIV) reverse transcriptase, retroviral reverse transcriptase, retrotransposon reverse transcriptase, hepatitis B reverse transcriptase, cauliflower mosaic virus reverse transcriptase, bacterial reverse transcriptase, *Thermus thennophilus* (Tth) DNA polymerase, *Thermus aquaticus* (Taq) DNA polymerase, *Thermotoga neopolitana* (Tne) DNA polymerase, *Thermotogamaritima* (Tma) DNA polymerase, *Thermococcus litoralis* (Tli, e.g., VENT® brand) DNA polymerase, *Pyrococcus furiosus* (Pfu) DNA polymerase, *Pyrococcus* species GB-D (e.g., DEEPVENT™ brand) DNA polymerase, *Pyrococcus woosii* (Pwo) DNA polymerase, *Bacillus sterothermophilus* (Bst) DNA polymerase, *Sulfolobus acidocaldarius* (Sac) DNA polymerase, *Thermoplasma acidophilum* (Tac) DNA polymerase, *Thermus favus* (Tfl/Tub) DNA polymerase, *Thermus ruber* (Tru) DNA polymerase, *Thermus brockianus* (e.g., DYNAZYME® brand) DNA polymerase, *Methanobacterium thermoautotrophicuin* (Mth) DNA polymerase, and mutants, variants and derivatives thereof. Particularly preferred for use in the invention are the variants of these enzymes that are substantially reduced in RNase H activity. Preferred reverse transcriptases for use in the invention include SUPERSCRIPT™, SUPERSCRIPT™ II and THERMOSCRIPT™ brands of reverse transcriptases available from the Life Technologies Division of Invitrogen Corporation (Rockville, Md.), and other reverse transcriptases described in U.S. Pat. No. 5,244,797 and WO 98/47912. By an enzyme "substantially reduced in RNase H activity" is meant that the enzyme has less than about 20%, more preferably less than about 15%, 10% or 5%, and most preferably less than about 2%, of the RNase H activity of a wildtype or "RNase H+" enzyme such as wildtype M-MLV or AMV reverse transcriptases. The RNase H activity of any enzyme may be determined by a variety of assays, such as those described, for example, in U.S. Pat. No. 5,244,797, in Kotewicz, M. L., et al., *Nucl. Acids Res.* 16:265 (1988) and in Gerard, G. F., et al., *FOCUS* 14(5):91 (1992), the disclosures of all of which are fully incorporated herein by reference.

The invention is thus directed to methods for making one or more nucleic acid molecules, comprising mixing one or more nucleic acid templates (preferably one or more RNA templates and most preferably one or more messenger RNA templates) with one or more polypeptides having reverse transcriptase activity and incubating the mixture under conditions sufficient to make one or more first nucleic acid molecules complementary to all or a portion of the one or more nucleic acid templates. Such conditions preferably comprise the use of one or more primers (preferably oligo dT) and one or more nucleotides. In a preferred embodiment, the first nucleic acid molecule is a single-stranded cDNA. Nucleic acid templates suitable for reverse transcription according to this aspect of the invention include any nucleic acid molecule or population of nucleic acid molecules (preferably RNA and most preferably mRNA), particularly those derived from a cell or tissue. In a preferred aspect, a population of mRNA molecules (a number of different mRNA molecules, typically obtained from cells or tissue) are used to make a cDNA library, in accordance with the invention. Preferred cellular sources of nucleic acid templates include bacterial cells, fungal cells, plant cells and animal cells.

The invention also concerns methods for making one or more double-stranded nucleic acid molecules. Such methods comprise (a) mixing one or more nucleic acid templates (preferably RNA or mRNA, and more preferably a population of mRNA templates) with one or more polypeptides having reverse transcriptase activity; (b) incubating the mixture under conditions sufficient to make one or more first nucleic acid molecules complementary to all or a portion of the one or more templates; and (c) incubating the first nucleic acid molecules under conditions sufficient to make one or more second nucleic acid molecules complementary to all or a portion of the first nucleic acid molecules, thereby forming one or more double-stranded nucleic acid molecules comprising the first and second nucleic acid molecules. Such methods may include the use of one or more DNA polymerases (and preferably one or more primers and nucleotides) as part of the process of making the one or more double-stranded nucleic acid molecules.

The invention also relates to methods for amplifying a nucleic acid molecule. Such amplification methods comprise mixing the double-stranded nucleic acid molecules produced as described above with one or more DNA polymerases and incubating the mixture under conditions sufficient to amplify the double-stranded nucleic acid molecule. In a first preferred embodiment, the invention concerns a method for amplifying one or more nucleic acid molecules, the method comprising (a) mixing one or more nucleic acid templates (preferably one or more RNA or mRNA templates and more preferably a population of mRNA templates) with one or more polypeptides having reverse transcriptase activity and with one or more DNA polymerases and (b) incubating the mixture under conditions sufficient to amplify nucleic acid molecules complementary to all or a portion of the one or more templates.

The invention is also directed to nucleic acid molecules (particularly single- or double-stranded cDNA molecules) or amplified nucleic acid molecules produced according to the above-described methods and to vectors (particularly expression vectors) comprising these nucleic acid molecules or amplified nucleic acid molecules.

The invention is further directed to compositions made or prepared while carrying out the methods of the invention. Such compositions may comprise the solid support of the invention, one or more mRNA molecules and/or one or more cDNA molecules produced from said mRNA molecules.

The invention is also directed to kits for use in the methods of the invention. Such kits can be used for making or amplifying nucleic acid molecules (single- or double-stranded) according to the invention. The kits of the invention comprise a carrier, such as a box or carton, having in close confinement therein one or more containers, such as vials, tubes, bottles and the like. Kits of the invention may comprise one or more of the reverse transcriptase enzymes (preferably one or more such enzymes that are reduced or substantially reduced in RNase H activity), one or more solid supports, one or more primers, one or more nucleotides and one or more reaction buffers. The kits of the invention may also comprise instructions for carrying out the methods of the invention.

Other preferred embodiments of the present invention will be apparent to one of ordinary skill in light of the following drawings and description of the invention, and of the claims.

BRIEF DESCRIPTION OF THE DRAWINGS

FIG. 1 shows the results of a Northern blot analysis of RNA stored and eluted from a solid support.

DETAILED DESCRIPTION OF THE INVENTION

Definitions

Figure 2A:
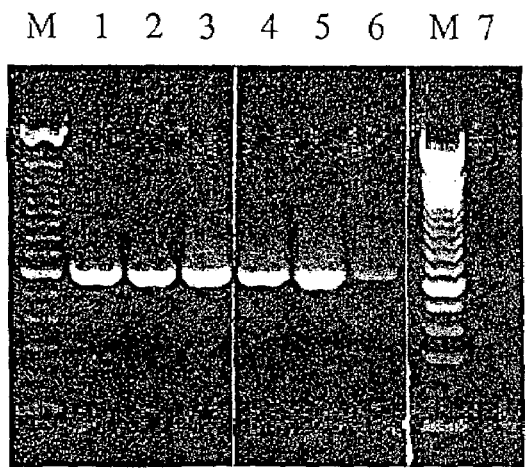
FIG. 2 shows the results of an RT-PCR analysis of RNA stored and eluted from a solid support using samples derived from HeLa cells.

In the description that follows, a number of terms used in recombinant DNA technology are utilized extensively. In order to provide a clear and more consistent understanding of the specification and claims, including the scope to be given such terms, the following definitions are provided.

Amplification. As used herein, "amplification" refers to any in vitro method for increasing the number of copies of a nucleotide sequence with the use of a polymerase. Nucleic acid amplification results in the incorporation of nucleotides into a nucleic acid (e.g., DNA) molecule or primer thereby forming a new nucleic acid molecule complementary to the nucleic acid template. The formed nucleic acid molecule and its template can be used as templates to synthesize additional nucleic acid molecules. As used herein, one amplification reaction may consist of many rounds of nucleic acid synthesis. Amplification reactions include, for example, polymerase chain reactions (PCR). One PCR reaction may consist of 5 to 100 "cycles" of denaturation and synthesis of a nucleic acid molecule.

Polymerases (including DNA polymerases and RNA polymerases) useful in accordance with the present invention include, but are not limited to, *Thermus thermophilus* (Tth) DNA polymerase, *Thermus aquaticus* (Taq) DNA polymerase, *Thermotoga neopolitana* (Tne) DNA polymerase, *Thermotoga maritima* (Tma) DNA polymerase, *Thermococcus litoralis* (Tli, e.g., VENT® brand) DNA polymerase, *Pyrococcus furiosus* (Pfu) DNA polymerase, *Pyrococcus* species GB-D (e.g., DEEPVENT™ brand) DNA polymerase, *Pyrococcus woosii* (Pwo) DNA polymerase, *Bacillus sterothermophilus* (Bst) DNA polymerase, *Bacillus caldophilus* (Bca) DNA polymerase, *Sulfolobus acidocaldarius* (Sac) DNA polymerase, *Thermoplasma acidophilian* (Tac) DNA polymerase, *Thennus flavus* (Tfl/Tub) DNA polymerase, *Thernius ruber* (Tru) DNA polymerase, *Thermus brockianus* (DYNAZYME™) DNA polymerase, *Methanobacterium thermoautotrophicion* (Mth) DNA polymerase, mycobacterium DNA polymerase (Mtb, Mlep), and mutants, and variants and derivatives thereof. RNA polymerases such as T3, T5 and SP6 and mutants, variants and derivatives thereof may also be used in accordance with the invention.

Polymerases used in accordance with the invention may be any enzyme that can synthesize a nucleic acid molecule from a nucleic acid template, typically in the 5' to 3' direction. The nucleic acid polymerases used in the present invention may be mesophilic or thermophilic, and are preferably thermophilic. Preferred mesophilic DNA polymerases include T7 DNA polymerase, T5 DNA polymerase, Klenow fragment DNA polymerase, DNA polymerase III and the like. Preferred thermostable DNA polymerases that may be used in the methods of the invention include Taq, Tne, Tma, Pfu, Tfl, Tth, Stoffel fragment, Tli (e.g., VENT® brand) and *Pyrococcus* species GB-D DNA (e.g., DEEP-VENT™ brand) polymerases, and mutants, variants and derivatives thereof (U.S. Pat. No. 5,436,149; U.S. Pat. No. 4,889,818; U.S. Pat. No. 4,965,188; U.S. Pat. No. 5,079,352; U.S. Pat. No. 5,614,365; U.S. Pat. No. 5,374,553; U.S. Pat. No. 5,270,179; U.S. Pat. No. 5,047,342; U.S. Pat. No. 5,512,462; WO 92/06188; WO 92/06200; WO 96/10640; Barnes, W. M., *Gene* 112:29–35 (1992); Lawyer, F. C., et al., *PCR Meth. Appl.* 2:275–287 (1993); Flaman, J.-M, et al., *Nuc. Acids Res.* 22(15):3259–3260 (1994)). For amplification of long nucleic acid molecules (e.g., nucleic acid molecules longer than about 3–5 Kb in length), at least two DNA polymerases (one substantially lacking 3' exonuclease activity and the other having 3'exonuclease activity) are typically used. See U.S. Pat. No. 5,436,149; and U.S. Pat. No. 5,512,462; Barnes, W. M., *Gene* 112:29–35 (1992), the disclosures of which are incorporated herein in their entireties. Examples of DNA polymerases substantially lacking in 3' exonuclease activity include, but are not limited to, Taq, Tne(exo⁻), Tma(exo⁻), Pfu(exo⁻), Pwo(exo⁻) and Tth DNA polymerases, and mutants, variants and derivatives thereof.

Host Cell. Any prokaryotic or eukaryotic cell. Such cell may be the recipient of a replicable expression vector or cloning vector. The terms "host" or "host cell" or "cell" may be used interchangeably herein. For examples of such hosts, see Maniatis et al., *Molecular Cloning: A Laboratory Manual*, Cold Spring Harbor Laboratory, Cold Spring Harbor, N.Y. (1982). Preferred prokaryotic hosts include, but are not limited to, bacteria of the genus *Escherichia* (e.g. *E. coli*), *Bacillus, Staphylococcus, Agrobacter* (e.g. *A. tumefaciens*), *Streptomyces, Pseudomonas, Salmonella, Serratia, Caryophanon*, etc. The most preferred prokaryotic host is *E. coli*. Bacterial hosts of particular interest in the present invention include *E. coli* K12, DH10B, DH5a and HB101. Preferred eukaryotic hosts include, but are not limited to, fungi, fish cells, yeast cells, plant cells and animal cells. Particularly preferred animal cells are insect cells such as *Drosophila* cells, *Spodoptera* Sf9 and Sf21 cells and *Trichoplusa* High-Five cells; nematode cells such as *C. elegans* cells; and mammalian cells such as COS cells, CHO cells, VERO cells, 293 cells, PERC6 cells, BHK cells and human cells.

Vector. A vector is a nucleic acid molecule (preferably DNA) capable of replicating autonomously in a host cell. Such vectors may also be characterized by having a small number of endonuclease restriction sites at which such sequences may be cut without loss of an essential biological function and into which nucleic acid molecules may be spliced to bring about its replication and cloning. Examples include plasmids, autonomously replicating sequences (ARS), centromeres, cosmids and phagemids. Vectors can further provide primer sites, e.g., for PCR, transcriptional and/or translational initiation and/or regulation sites, recombinational signals, replicons, etc. The vector can further contain one or more selectable markers suitable for use in the identification of cells transformed or transfected with the vector, such as kanamycin, tetracycline, amplicillin, etc.

In accordance with the invention, any vector may be used. In particular, vectors known in the art and those commercially available (and variants or derivatives thereof) may be used in accordance with the invention. Such vectors may be obtained from, for example, Vector Laboratories Inc., Invitrogen, Promega, Novagen, NEB, Clontech, Boehringer Mannheim, Pharmacia, EpiCenter, OnGenes Technologies Inc., Stratagene, Perkin Elmer, Pharmingen, Life Technologies, Inc., and Research Genetics. Such vectors may then for example be used for cloning or subcloning nucleic acid molecules of interest. General classes of vectors of particular interest include prokaryotic and/or eukaryotic cloning vectors, expression vectors, fusion vectors, two-hybrid or reverse two-hybrid vectors, shuttle vectors for use in different hosts, mutagenesis vectors, transcription vectors, vectors for receiving large inserts and the like.

Other vectors of interest include viral origin vectors (M13 vectors, bacterial phage 1 vectors, baculovirus vectors, adenovirus vectors, and retrovirus vectors), high, low and adjustable copy number vectors, vectors which have compatible replicons for use in combination in a single host (pACYC 184 and pBR322) and eukaryotic episomal replication vectors (pCDM8).

Storage. As used herein, "storage" refers to maintaining the support/nucleic acids for a period of time at a temperature or temperatures of interest. Preferably, storage is accomplished at about 20 to 30° C. (preferably room temperature, e.g. 25° C.), but may be at higher or lower temperatures depending on the need. Lower storage temperatures may range from about 0 to 20° C., −20 to 0° C., and −80 to −20° C. Long term storage in accordance with the invention is greater than one year, preferably greater than 2 years, still more preferably greater than 3 years, still more preferably greater than 5 years, still more preferably greater than 10 years, and most preferably greater than 15 years.

Other terms used in the fields of recombinant DNA technology and molecular and cell biology as used herein will be generally understood by one of ordinary sill in the applicable arts.

Production of cDNA Molecules

Sources of Nucleic Acid Molecules

In accordance with the invention, cDNA molecules (single-stranded or double-stranded) may be prepared from a variety of nucleic acid template molecules. Preferred nucleic acid molecules for use in the present invention include single-stranded or double-stranded DNA and RNA molecules, as well as double-stranded DNA:RNA hybrids. More preferred nucleic acid molecules include messenger RNA (mRNA), transfer RNA (tRNA) and ribosomal RNA (rRNA) molecules, although mRNA molecules are the preferred template according to the invention.

The nucleic acid molecules that are used to prepare cDNA molecules according to the methods of the present invention may be prepared synthetically according to standard organic chemical synthesis methods that will be familiar to one of ordinary skill. More preferably, the nucleic acid molecules may be obtained from natural sources, such as a variety of cells, tissues, organs or organisms. Cells that may be used as sources of nucleic acid molecules may be prokaryotic (bacterial cells, including but not limited to those of species of the genera *Escherichia, Bacillus, Serratia, Salmonella, Staphylococcus, Streptococcus, Clostridium, Chlamydia, Neisseria, Treponema, Mycoplasma, Borrelia, Legionella, Pseudomonas, Mycobacterium, Helicobacter, Erwinia, Agrobacterium, Rhizobium, Xanthomonas* and *Streptomyces*) or eukaryotic (including fungi (especially yeasts), plants, protozoans and other parasites, and animals including insects including but not limited to *Drosophila* spp. cells, *Spodoptera* Sf9 and Sf21 cells and *Trichoplusa* High-Five cells; nematodes (particularly *Caenorhabditis elegans* cells), and mammals such as COS cells, CHO cells, VERO cells, 293 cells, PERC6 cells, BHK cells, and other mouse and human cells. In some preferred embodiments, the nucleic acids stored according to the present invention may be derived from viruses.

Mammalian somatic cells that may be used as sources of nucleic acids include blood cells (reticulocytes and leukocytes), endothelial cells, epithelial cells, neuronal cells (from the central or peripheral nervous systems), muscle cells (including myocytes and myoblasts from skeletal, smooth or cardiac muscle), connective tissue cells (including fibroblasts, adipocytes, chondrocytes, chondroblasts, osteocytes and osteoblasts) and other stromal cells (e.g., macrophages, dendritic cells, Schwann cells). Mammalian germ cells (spermatocytes and oocytes) may also be used as sources of nucleic acids for use in the invention, as may the progenitors, precursors and stem cells that give rise to the above somatic and germ cells. Also suitable for use as nucleic acid sources are mammalian tissues or organs such as those derived from brain, kidney, liver, pancreas, blood, bone marrow, muscle, nervous, skin, genitourinary, circulatory, lymphoid, gastrointestinal and connective tissue sources, as well as those derived from a mammalian (including human) embryo or fetus.

Any of the above prokaryotic or eukaryotic cells, tissues and organs may be normal, diseased, transformed, established, progenitors, precursors, fetal or embryonic. Diseased cells may, for example, include those involved in infectious diseases (caused by bacteria, fungi or yeast, viruses (including AIDS, HIV, HTLV, herpes, hepatitis and the like) or parasites), in genetic or biochemical pathologies (e.g., cystic fibrosis, hemophilia, Alzheimer's disease, muscular dystrophy or multiple sclerosis) or in cancerous processes. Transformed or established animal cell lines may include, for example, COS cells, CHO cells, VERO cells, BHK cells, HeLa cells, HepG2 cells, K562 cells, 293 cells, L929 cells, F9 cells, and the like. Other cells, cell lines, tissues, organs and organisms suitable as sources of nucleic acids for use in the present invention will be apparent to one of ordinary skill in the art.

Once the starting cells, tissues, organs or other samples are obtained, nucleic acid molecules (such as mRNA) may optionally be isolated therefrom by methods that are well-known in the art (See, e.g., Maniatis, T., et al., *Cell* 15:687–701 (1978); Okayama, H., and Berg, P., *Mol. Cell. Biol.* 2:161–170 (1982); Gubler, U., and Hoffman, B. J., *Gene* 25:263–269 (1983)). The nucleic acid molecules thus isolated may then be contacted directly with the solid supports of the invention. Alternatively, cells, tissues, etc., may be contacted directly with the support.

In the practice of the invention, cDNA molecules or cDNA libraries are produced by mixing one or more nucleic acid molecules obtained as described above, which is preferably one or more mRNA molecules such as a population of mRNA molecules, with one or more polypeptides having reverse transcriptase activity under conditions favoring the reverse transcription of the nucleic acid molecule by the action of the enzymes to form one or more cDNA molecules (single-stranded or double-stranded). Thus, the method of the invention comprises (a) mixing one or more nucleic acid templates (preferably one or more RNA or mRNA templates, such as a population of mRNA molecules) with one or more reverse transcriptases and (b) incubating the mixture under conditions sufficient to make one or more nucleic acid molecules complementary to all or a portion of the one or more templates. Such methods may include the use of one or more DNA polymerases. The invention may be used in conjunction with methods of cDNA synthesis such as those described in the Examples below, or others that are well-known in the art (see, e.g., Gubler, U., and Hoffman, B. J., *Gene* 25:263–269 (1983); Krug, M. S., and Berger, S. L., *Meth. Enzymol.* 152:316–325 (1987); Sambrook, J., et al., *Molecular Cloning: A Laboratory Manual*, 2nd ed., Cold Spring Harbor, N.Y.: Cold Spring Harbor Laboratory Press, pp. 8.60–8.63 (1989); and WO 98/51699), to produce cDNA molecules or libraries. In a preferred embodiment, the cDNA may be produced using the methods detailed in U.S. patent application Ser. No. 09/076,115 and/or U.S. provisional application Ser. No. 60/122,395 filed Mar. 2, 1999.

Other methods of cDNA synthesis which may advantageously use the present invention will be readily apparent to one of ordinary skill in the art.

Having obtained cDNA molecules or libraries according to the present methods, these cDNAs may be isolated for further analysis or manipulation. Detailed methodologies for purification of cDNAs are taught in the GENETRAPPER™ manual (Life Technologies, Inc.; Rockville, Md.), which is incorporated herein by reference in its entirety, although alternative standard techniques of cDNA isolation known in the art may be used (see, e.g., Sambrook, J., et al., *Molecular Cloning: A Laboratory Manual*, 2nd ed., Cold Spring Harbor, N.Y.: Cold Spring Harbor Laboratory Press, pp. 8.60–8.63 (1989)).

In other aspects of the invention, the invention may be used in methods for amplifying nucleic acid molecules. Nucleic acid amplification methods according to this aspect of the invention may be one-step (e.g., one-step RT-PCR) or two-step (e.g., two-step RT-PCR) reactions. According to the invention, one-step RT-PCR type reactions may be accomplished in one tube thereby lowering the possibility of contamination. Such one-step reactions comprise (a) mixing a nucleic acid template (e.g., mRNA) with one or more polypeptides having reverse transcriptase activity and with one or more DNA polymerases and (b) incubating the mixture under conditions sufficient to amplify a nucleic acid molecule complementary to all or a portion of the template. Alternatively, amplification may be accomplished by mixing a template with one or more polypeptides having reverse transcriptase activity (and optionally having DNA polymerase activity). Incubating such a reaction mixture under appropriate conditions allows amplification of a nucleic acid molecule complementary to all or a portion of the template. Such amplification may be accomplished by the reverse transcriptase activity alone or in combination with the DNA polymerase activity. Two-step RT-PCR reactions may be accomplished in two separate steps. Such a method comprises (a) mixing a nucleic acid template (e.g., mRNA) with one or more reverse transcriptases, (b) incubating the mixture under conditions sufficient to make a nucleic acid molecule (e.g., a DNA molecule) complementary to all or a portion of the template, (c) mixing the nucleic acid molecule with one or more DNA polymerases and (d) incubating the mixture of step (c) under conditions sufficient to amplify the nucleic acid molecule. For amplification of long nucleic acid molecules (i.e., greater than about 3–5 Kb in length), a combination of DNA polymerases may be used, such as one DNA polymerase having 3' exonuclease activity and another DNA polymerase being substantially reduced in 3' exonuclease activity. An alternative two-step procedure comprises the use of one or more polypeptides having reverse transcriptase activity and DNA polymerase activity (e.g., Tth, Tma or Tne DNA polymerases and the like) rather than separate addition of a reverse transcriptase and a DNA polymerase.

Amplification methods which may be used in accordance with the present invention include PCR (U.S. Pat. Nos. 4,683,195 and 4,683,202), Strand Displacement Amplification (SDA; U.S. Pat. No. 5,455,166; EP 0 684 315), and Nucleic Acid Sequence-Based Amplification (NASBA; U.S. Pat. No. 5,409,818; EP 0 329 822).

Kits

In another embodiment, the present invention may be assembled into kits for use in reverse transcription or amplification of a nucleic acid molecule. Kits according to this aspect of the invention comprise a carrier means, such as a box, carton, tube or the like, having in close confinement therein one or more container means, such as vials, tubes, ampules, bottles and the like. The kits of the invention may comprise one or more components selected from one or more reverse transcriptases, one or more DNA polymerases, one or more suitable buffers, one or more nucleotides, one or more solid supports (particularly FTA® or derivatives or variants thereof) and/or one or more primers.

In a specific aspect of the invention, the reverse transcription and amplification kits may comprise one or more components (in mixtures or separately) including one or more, polypeptides having reverse transcriptase activity, one or more supports, one or more nucleotides needed for synthesis of a nucleic acid molecule, and/or one or more primers (e.g., oligo(dT) for reverse transcription). Such reverse transcription and amplification kits may further comprise one or more DNA polymerases. Preferred polypeptides having reverse transcriptase activity, DNA polymerases, nucleotides, primers and other components suitable for use in the reverse transcription and amplification kits of the invention include those described above. The kits encompassed by this aspect of the present invention may further comprise additional reagents and compounds necessary for carrying out standard nucleic acid reverse transcription or amplification protocols. Such polypeptides having reverse transcriptase activity, DNA polymerases, nucleotides, primers, and additional reagents, components or compounds may be contained in one or more containers, and may be contained in such containers in a mixture of two or more of the above-noted components or may be contained in the kits of the invention in separate containers.

Use of Nucleic Acid Molecules

The nucleic acid molecules or cDNA libraries prepared by the methods of the present invention may be further characterized, for example by cloning and sequencing (i.e., determining the nucleotide sequence of the nucleic acid molecule), or by the sequencing methods (see, e.g., U.S. Pat. Nos. 4,962,022 and 5,498,523, which are directed to methods of DNA sequencing). Alternatively, these nucleic acid molecules may be used for RPA, northern blots or attachment to chips for the manufacture of various materials in industrial processes, such as hybridization probes by methods that are well-known in the art. Production of hybridization probes from cDNAs will, for example, provide the ability for those in the medical field to examine a patient's cells or tissues for the presence of a particular genetic marker such as a marker of cancer, of an infectious or genetic disease, or a marker of embryonic development. Furthermore, such hybridization probes can be used to isolate DNA fragments from genomic DNA or cDNA libraries prepared from a different cell, tissue or organism for further characterization.

The nucleic acid molecules of the present invention may also be used to prepare compositions for use in recombinant DNA methodologies. Accordingly, the present invention relates to recombinant vectors which comprise the cDNA or amplified nucleic acid molecules of the present invention, to host cells which are genetically engineered with the recombinant vectors, to methods for the production of a recombinant polypeptide using these vectors and host cells, and to recombinant polypeptides produced using these methods.

Recombinant vectors may be produced according to this aspect of the invention by inserting, using methods that are well-known in the art, one or more of the cDNA molecules or amplified nucleic acid molecules prepared according to the present methods into a vector. The vector used in this aspect of the invention may be, for example, a phage or a plasmid, and is preferably a plasmid. Preferred are vectors comprising cis-acting control regions to the nucleic acid encoding the polypeptide of interest. Appropriate trans-acting factors may be supplied by the host, supplied by a complementing vector or supplied by the vector itself upon introduction into the host.

In certain preferred embodiments in this regard, the vectors provide for specific expression (and are therefore termed "expression vectors"), which may be inducible and/or cell type-specific. Particularly preferred among such vectors are those inducible by environmental factors that are easy to manipulate, such as temperature and nutrient additives.

Expression vectors useful in the present invention include chromosomal-, episomal- and virus-derived vectors, e.g., vectors derived from bacterial plasmids or bacteriophages, and vectors derived from combinations thereof, such as cosmids and phagemids, and will preferably include at least one selectable marker such as a tetracycline or ampicillin resistance gene for culturing in a bacterial host cell. Prior to insertion into such an expression vector, the cDNA or amplified nucleic acid molecules of the invention should be operatively linked to an appropriate promoter, such as the phage lambda $P_L$ promoter, the *E. coli* i lac, trp and tac promoters. Other suitable promoters will be known to the skilled artisan.

Among vectors preferred for use in the present invention include pQE70, pQE60 and pQE-9, available from Qiagen; pBS vectors, Phagescript vectors, Bluescript vectors, pNH8A, pNH16a, pNH18A, pNH46A, available from Stratagene; pcDNA3 available from Invitrogen; pGEX, pTrxfus, pTrc99a, pET-5, pET-9, pKK223-3, pKK233-3, pDR540, pRIT5 available from Pharmacia; and pSPORT1, pSPORT2 and pSV-SPORTI and Gateway™ Vectors, available from Life Technologies, Inc. Other suitable vectors will be readily apparent to the skilled artisan.

The invention also provides methods of producing a recombinant host cell comprising the cDNA molecules, amplified nucleic acid molecules or recombinant vectors of the invention, as well as host cells produced by such methods. Representative host cells (prokaryotic or eukaryotic) that may be produced according to the invention include, but are not limited to, bacterial cells, yeast cells, plant cells and animal cells. Preferred bacterial host cells include *Escherichia coli* cells (most particularly *E. coli* strains DHIOB and Stbl2, which are available commercially (Life Technologies, Inc; Rockville, Md.)), *Bacillus subtilis* cells, *Bacillus megaterium* cells, *Streptomyces* spp. cells, *Erwinia* spp. cells, *Klebsiella* spp. cells and *Salmonella typhimurium* cells. Preferred animal host cells include insect cells (most particularly *Spodoptera frugiperda* Sf9 and Sf21 cells and *Trichoplusa* High-Five cells) and mammalian cells (most particularly CHO, COS, VERO, BHK and human cells). Such host cells may be prepared by well-known transformation, electroporation or transfection techniques that will be familiar to one of ordinary skill in the art.

In addition, the invention provides methods for producing a recombinant polypeptide, and polypeptides produced by these methods. According to this aspect of the invention, a recombinant polypeptide may be produced by culturing any of the above recombinant host cells under conditions favoring production of a polypeptide therefrom, and isolation of the polypeptide. Methods for culturing recombinant host cells, and for production and isolation of polypeptides therefrom, are well-known to one of ordinary skill in the art.

It will be readily apparent to one of ordinary skill in the relevant arts that other suitable modifications and adaptations to the methods and applications described herein are obvious and may be made without departing from the scope of the invention or any embodiment thereof. Having now described the present invention in detail, the same will be more clearly understood by reference to the following examples, which are included herewith for purposes of illustration only and are not intended to be limiting of the invention.

EXAMPLES

All reagents and media were from Life Technologies, Inc, Rockville, Md. unless otherwise stated.

Example 1

Preparation and Storage of Nucleic Acids on Solid Supports Cell Culture

HeLa cells were grown in suspension in S-MEM with 10% heat-inactivated horse serum and 4 mM glutamine and BHK-21 cells were grown in monolayer as described (7) and suspensions were prepared by trypsinization followed by washing and resuspension in Dulbecco's PBS (containing $Ca^{2+}$ and $Mg^{2+}$), at the appropriate cell density. Resuspended cells were spotted on FTA® GeneCards using an adjustable pipettor and similar control samples were vialed and quick frozen in a dry-ice ethanol bath and stored at $-70°$ C.

Preparation and storage of samples. 20 µl of blood and 5 µl of HeLa cell suspension ($1 \times 10^7$ cells/ml) were spotted directly on FTA® GeneCards, allowed to air dry for up to 2 h, and stored at room temperature, 4° C., $-20°$ C., or $-70°$ C. in sealed foil packages containing desiccant. Gene Guard Swabs containing buccal cells were applied onto FTA® GeneCards, allowed to air dry for up to 2 hours and stored at room temperature in sealed foil packages with desiccant. Plants were grown in soil and leaf samples were obtained. Plant leaf samples were pressed onto FTA® GeneCards using a nitrogen-driven press (17.5 psi) and treated as described above.

Example 2

Isolation of Poly($A^+$)RNA Directly from Cells on FTA® Paper

20–50 µl of a BHK-21 cell suspension ($4.25 \times 10^7$/ml) was spotted directly onto FTA® GeneCards and stored at $-70°$ C. as described above or placed in tube, frozen in dry ice ethanol and placed at $-70°$ C. For RNA isolation, the entire spot was cut into small pieces using a razor blade and added to 750 µl of sterile water followed by incubation at room temperature for 15 min with frequent vortexing. To remove the filter pieces, the eluate was passed through a shredder microfuge tube (Qiagen, CA) and the poly(A+) RNA isolated by selection with oligonucleotide(dT). Typical yields from these samples were 300 ng mRNA/$2 \times 10^6$ cells. Total RNA from BHK-cells was isolated using TRIzol™ Reagent according to the manufacturer's directions and poly($A^+$) RNA was isolated from these samples by selection with oligo(dT).

Example 3

Northern Blot Analysis of RNA

Total RNA and Poly($A^+$)RNA were subjected to electrophoresis in a 1.5%, 1× MOPS, 30% formaldehyde agarose gel as described (8) followed by transfer to a nylon membrane. The blot was baked at 80° C. for 1 h followed by prehybridization as described (8). $^{32}$P-labeled b-actin probe was prepared using the RadPrime kit (Life Technologies, Inc) and was adjusted to a final concentration of $5 \times 10^6$ cpm/ml hybridization buffer. Hybridization was performed as described (8) for 16 h at 42° C. The blot was washed 3×5 min with 2×SSC containing 0.1% SDS at room temperature and 2×30 min with 0.25×SSC containing 0.1% SDS at 65° C. The blot was then placed in plastic wrap and exposed to X-ray film.

The results of the Northern blot analysis are shown in FIG. 1. Total RNA (lane 1) was isolated from BHK-21 cells using TRIzol Reagent. Poly(A+)RNA was isolated from the total RNA (lanes 2–3) or directly from BHK-21 cells applied to the FTA® GeneCard (lanes 4–5) as described above. The number of cells used was $2.5 \times 10^6$ (lanes 2 and 4) and $4 \times 10^6$ (lanes 1, 3 and 5).

The quality and intensity of the 2.2-kb signal from the FTA® archived samples is directly comparable to that of RNA isolated from vialed BHK-21 cells by traditional means. Based on these results, it appears that the integrity of poly(A+)RNA from mammalian cell samples spotted onto FTA® GeneCards is maintained. However, is has been found that after application of mammalian cells onto FTA® paper, the samples must be placed at temperatures $\leq -20°$ C. for long term storage (greater than 1 month). RNA integrity in samples stored at room temperature or 4° C. for extended periods was sub-optimal compared to controls. Genomic DNA contained in FTA®-archived samples stored at room temperature for up to 7.5 years has been shown to be intact (9), which is quite different from our observations with RNA.

Example 4

Amplification of Nucleic Acids

PCR of genomic DNA. Using a HARRIS MICRO-PUNCH®, 2-mm punches were removed from the center of the biological sample spot, placed in a 1.5 ml microfuge tube and processed by washing 3×5 min with FTA® Purification Reagent (Life Technologies Inc.) at room temperature followed by 2×5 min washes with TE (10 mm Tris-HCl pH 8.0, and 0.1 mM EDTA) at room temperature. Each punch was processed individually and then transferred to a thin-walled amplification tube. Amplification was performed by using PLATINUM® Taq High Fidelity DNA polymerase (IU), in 1× PLATINUM® Taq High Fidelity PCR Buffer, 200 mM dNTPs, 200 nM primers, and 2 mM MgSO$_4$. The sequences of the primers used for the amplification reactions are shown in Table 1.

TABLE 1

Primer Sequences used.
(SEQ ID NOS.1–12,respectively in order of appearance)

| Target (Human) | Primer Sequences | Product size |
| --- | --- | --- |
| b-globin | Sense: 5'-CTGCAGTCCCAGGCTATTCAGG-3' | 1.3 kb |
| | Antisense: 5'-AGACTTGGACCATGACGGTGAT-3' | |
| b-globin | Sense: 5'-CTGCTGAAAGAGATGCGGTGG-3' | 3.19 kb |
| | Antisense: 5'-TCTTCCCAAAATGCCCTGAGT-3' | |
| Cysteine protease (plant) | Sense: , 5'-TCGCCGATCTGACTAATGAGGAG-3' | 1.05 kb |
| | Antisense: 5'-ATGCGCTTCATTGCCTTCACTCC-3' | |
| Replication protein A | Sense: 5'-CAAGATGTGGAACAGTGGATTC-3' | 1.08 kb |
| | Antisense: 5'-CATCTATCTTGATGTTGTAACAAGC-3' | |
| b-actin | Sense: 5'-CCTCGCCTTTGCCGATCC-3' | 0.626 kb |
| | Antisense: 5'-GGATCTTCATGAGGTAGTCAGTC-3' | |
| Clathrin-like protein | Sense: 5'-CCCAGTGACAGGAGGAGACCATA-3' | 5.76 kb |
| | Antisense: 5'-ATCCTGTGCTTTTTCTGTGGGAC-3' | |

RT-PCR. Using a HARRIS MICRO-PUNCH®, 2-mm punches were transferred to 1.5 ml low-binding RNase-free DNAse-free tubes (Marsh Biomedical) containing 400 µl of RNA processing buffer (10 mM Tris-HCl pH 8.0, 0.1 mM EDTA, 400–800 U/ml RNASEOUT® and 2 mM DTT) and incubated on ice for 25 min with vortexing every 5 min. In some experiments, the processing buffer also contained 250 µg/ml glycogen to facilitate subsequent precipitation of the RNA. Unlike genomic DNA, RNA elutes from the filter punches during this incubation. RT-PCR was done either directly using the processing buffer eluate as substrate or using RNA precipitated from the eluate. The RNA was precipitated by addition of salt (0.1 volumes of 3 M sodium acetate, or 0.5 volumes of 7.5 M ammonium acetate) and 0.5 volumes of ice cold 100% isopropanol. The samples were placed at −20° C. overnight, spun down at 12,000 rpm in the microfuge, washed with 75% ethanol (ice-cold) and allowed to air dry. RNA pellets were resuspended in 50 µl or 100 µl of sterile TE. Synthesis of first strand cDNA was performed using SUPERSCRIPT® It RNase H-RT (Life Technologies, Inc) in a final volume of 50 µl at 50° C. Amplification reactions (50 µl) contained ≦10 µl of the cDNA reaction and the following: 1× Amplification Buffer, 1.8 MM MgSO$_4$, 200 nM primers, 200 mM of each dNTP and 2.5 U of PLATINUM® Taq DNA polymerase. For templates larger than 4 kb, 1–2 U of PLATINUM® Taq DNA Polymerase High was used. Amplification products were analyzed by 1.2% TBE-OR 0.8% TAE agarose gel electrophoresis.

Figure 2B:
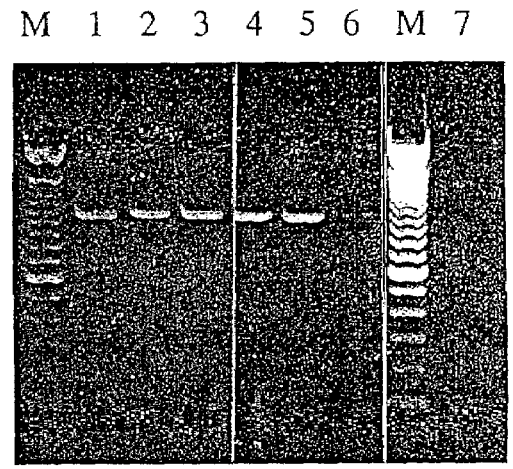
Figure 2C:
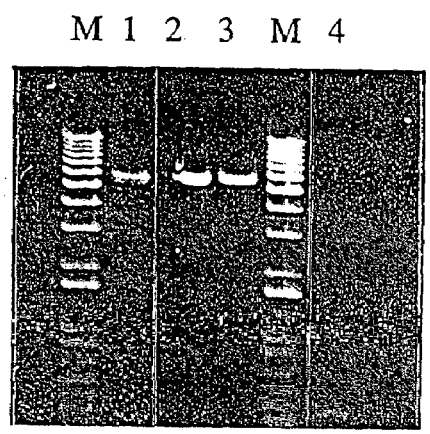
Figure 3:
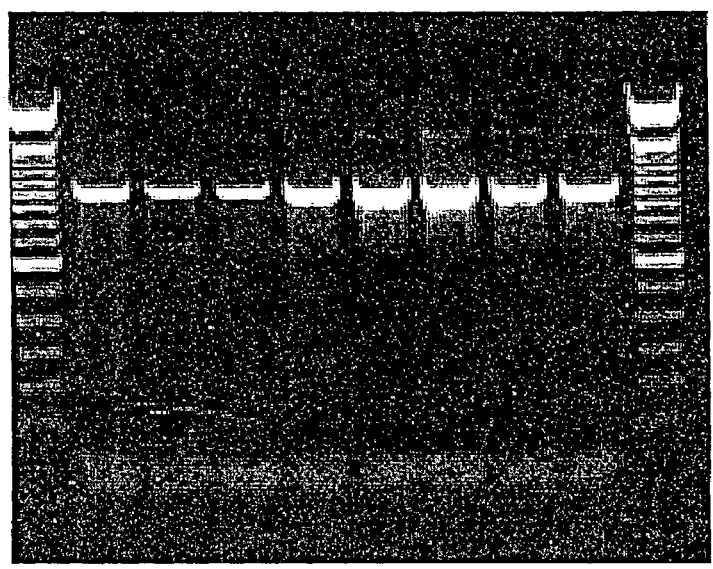
FIG. 3 shows the results of an RT-PCR analysis of RNA stored and eluted from a solid support using samples derived from plant cells.
Figure 4:
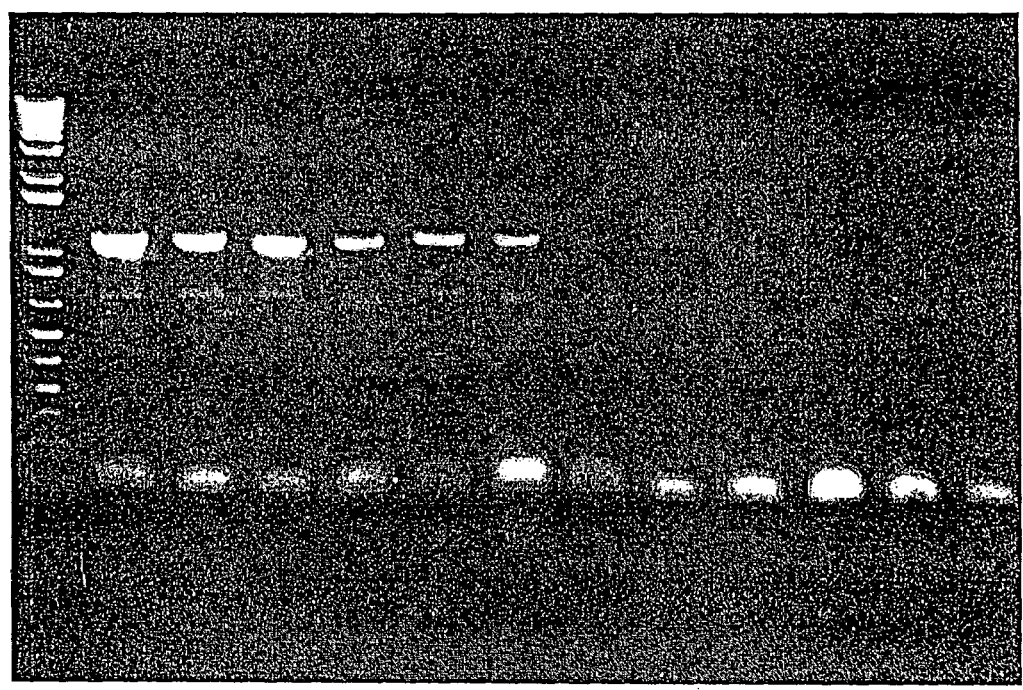
FIG. 4 shows the results of an RT-PCR analysis of RNA from varying amounts of cells stored and eluted from a solid support using samples derived from HeLa cells.

The results of the amplification of nucleic acids stored on solid supports are shown in FIGS. 2–4. FIG. 2 shows the results of the amplification of nucleic acids from HeLa cells. Eluted RNA was precipitated from washes taken from 2-mm punches of HeLa cell samples stored at −20° and −70° C. for 1 year as described above. The amplification targets were as follows: Panel A; a 626 bp sequence from b-actin mRNA was amplified using the following thermocycling conditions: 94° C. for 1 min, followed by 40 cycles of 94° C. for 30 s; 60° C. for 30 s and 72° C. for 1.5 min; forward and reverse primer sequences were 5'CCTCGCCTTTGC-CGATCC3' (SEQ ID NO: 9) and 5'GGATCTTCATGAGG-TAGTCAGTC3' (SEQ ID NO: 10), respectively. Panel B; a 1.08-kb sequence of RPA (replication protein A) mRNA was amplified using the following thermocycling conditions: 94° C. for 1 min, followed by 40 cycles of 94° C. for 30 s; 55° C. for 30 s and 72° C. for 1.5 min; forward and reverse primer sequences were 5'CAAGATGTGGAACAGTGGATTC3' (SEQ ID NO: 7) and 5'CATCTATCTTGATGTTGTAACAAGC3' (SEQ ID NO: 8), respectively.

and Panel C: a 5.76-kb sequence of a clathrin-like protein (D21260) mRNA was amplified using the following thermocycling conditions: 94° C. for 1 min, followed by 35 cycles of 94° C. for 20 s; 60° C. for 30 s and 68° C. for 7 min; forward and reverse primer sequences were 5'CCCAGTGACAGGAGGAGACCATA3' (SEQ ID NO: 11) and 5'ATCCTGTGCTTTTTCTGTGGGAC3' (SEQ ID NO: 12), respectively. For Panels A and B, Lanes 1–3 and 4–6 are from samples stored at −20° C. and −70° C., respectively subsequent to sample application onto FTA® GeneCards, whereas lane 7 is a negative control where SUPERSCRIPT II RT was omitted from the RT reaction. Lanes labeled M are a 1 kb ladder size markers. For Panel C, lanes 1, positive control, HeLa RNA, Lanes-2 and 3 are from samples stored at −70° C. subsequent to sample application onto FTA® GeneCards, whereas lane 4 is the negative control.

FIG. 3 shows the results of the amplification of nucleic acids from plant cells. RNA was eluted from 2-mm punches of the leaf samples from potato plants as described in above and 5 µl of the RNA eluate was added to each 50 ml RT reaction. The amplification target was a 1.05-kb sequence from a 1.8-kb cysteine protease (AJ003137) mRNA using the primers shown in Table 1. Thermocycling conditions were: 94° C. for 1 min, followed by 40 cycles of 94° C. for 30 s; 60° C. for 30 s; and 72° C. for 2 min. Lanes 1–3 and 4–7 are from samples stored at −20 C and −70 C, respectively subsequent to application on FTA® GeneCards, whereas lane 8 is a positive control where 50 ng of potato leaf RNA was added to the RT reaction.

The dependence of RT-PCR signal on amount of biological sample stored on card was examined and the results are shown in FIG. 4. 5 µl samples of suspensions of HeLa cells at different cell densities were spotted onto FTA® GeneCards, allowed to air dry for 1–2 hours and then stored at −70° C. for over 1 year. 2-mm punches were taken from the samples and treated as described above. An aliquot of the RNA (1/80th of the total volume of the wash) was used for RT-PCR as described in Methods. The target was a ~1.08 kb amplicon of the RPA (replication protein A gene, (M36951) using the primers indicated in Table 1 and the PCR conditions used in FIG. 2. Marker, 1 Kb Plus ladder. Lane 1–3, 25,000 cells; Lane 4–6, 5,000 cells; Lanes 7–9, 500 cells, Lanes 10–12 negative controls where SuperScript™ II RNase H-RT was omitted from the RT reaction.

RNA stability on FTA® GeneCards stored at temperatures ≦−20° C. was examined by performing RT-PCR analysis on different mRNA targets. In processing the FTA® punches, it was observed that unlike genomic DNA, RNA does not remain on the FTA® paper during processing. Virtually all of the RNA elutes into the initial wash, and this eluted cellular RNA can be directly placed into the first strand RT reaction or can be ethanol precipitated from the wash solution and resuspended in sterile water or TE prior to analysis. The results in FIGS. 2 and 3 demonstrate successful RT-PCR of different mRNA targets from mammalian cells and plant samples, respectively. For the mammalian cell samples, our RT-PCR targets were 626-bp, 1.08-kb and 5.76-kb sequences from b-actin (Panel A), replication protein A (RPA; Panel B) and clathrin-like protein (Panel C) mRNAs, respectively. For the potato leaf plant samples, our RT-PCR target consisted of a 852-bp sequence from the 1756-bp cysteine protease mRNA. Negative controls consisted of reactions where RT was omitted during the initial cDNA synthesis step (not shown for plant samples) and positive controls consisted of the addition of 100 ng of HeLa or 50 ng of plant leaf RNA directly to the initial cDNA synthesis step. It is important to include the negative control since we have observed that trace amounts of genomic DNA also elute from the punch during processing and it is necessary to ascertain that RT-PCR signals are indeed products from RNA and not contaminating genomic DNA. The results in FIGS. 2 and 3 demonstrate that the desired RNA-specific RT-PCR products were obtained with the FTA® samples stored at −20° C. and −70° C. and were comparable to the positive controls. We next examined the proportionality of RT-PCR signal obtained versus the number of HeLa cells that were spotted onto the FTA® GeneCard. Such an experiment would reveal the feasibility of using this method to semi-quantitatively measure differential gene expression in biological samples. HeLa cell suspensions at various densities were prepared and 5 µl aliquots of the various suspensions were identically spotted onto FT A® paper. The relative amount of RT-PCR product obtained was proportional to the number of cells placed onto the FTA® card (FIG. 4). These data indicate that at least semi-quantitatively, differences in mRNA levels can be measured by RT-PCR using FTA® Gene Cards.

Example 5 cDNA Library Construction from RNA Isolated from Biological Specimens Stored on FTA® Paper Poly(A+)RNA was directly isolated from 2.25×10⁶ BHK-21 cells stored on FTA® paper as described above except that the biotinylated oligonucleotide(dT) had special adapter sequences necessary for library construction. The primer inludes a Not I recognition site and has the sequence (Biotin)₄ GACTAGTTCTAGAT CGCGAGCGG CCGC-CCTTTTT TTTTTTTTTTTT TTTTTTTT (SEQ ID NO: 13); (see WO 98/51699 and U.S. application Ser. No. 09/076,115). As a positive control, poly(A+) RNA was isolated total RNA prepared by TRIzol reagent from the same number of cells. Double-stranded cDNA was made and cloned into plasmid vectors as described in WO 98/51699 and U.S. application Ser. No. 09/076,115. The number of primary clones obtained from the poly(A+)RNA was the same whether the mRNA was isolated directly from FTA® or from TRIzol-purified total RNA. The average insert size of the libraries was determined by colony PCR using primers to the plasmid vector. The average insert size for the FTA®-derived material was greater than that for the library constructed from the positive control poly(A+)RNA, 1000 bp vs 600 bp. This indicates that cDNA libraries of good quality can be made from mRNA isolated directly from samples stored on FTA®.

Having now fully described the present invention in some detail by way of illustration and example for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

REFERENCES

1. Burgoyne, L., Kijas, J., Hallsworh, P. and Turner, J. (1994) Proc. Fifth Int. Symp. Human Ident.
2. Belgrader, P., Del Rio, S. A., Turner, K. A., .Marino, M. A., Weaver, K. R. and Williams, P. E. (1995) Automated DNA purification and amplification from blood-stained cards using a robotic work-station. Biotechniques 19; 426–432
3. Del Rio, S. A., Marino, M. A. and Belgrader, P. (1996) Reusing the same blood-stained punch for sequential DNA amplifications and typing. Biotechniques 20: 970–974
4. Sitaraman, K., Darfler, M. and Westfall, B. (1999) Amplification of large DNA from Blood Stored at Room Temperature. FOCUS 21(1): 10
5. Hansen, P. and Blakesley, R. (1998) Simple Archiving of Bacterial and Plasmid DNAs for Future Use. FOCUS 20 (3): 72–74
6. Rogers, C. and Burgoyne, L. (1997) Bacterial typing: storing and processing of stabilized reference bacteria for polymerase chain reaction without preparing DNA—an example of an automatable procedure. Anal. Biochem. 247: 223–7
7. Ciccarone, V., Chu, Y., Schifferli, K., Pichet, J-P., Hawley-Nelson, P., Evans, K., Roy, L. and Bennett, S. (1999) LIPOFECTAMINE® 2000 Reagent for Rapid, Efficient Transfection of Eukaryotic Cells, FOCUS 21(2): 54–55
8. Sambrook, J., Fritsch, E. F. and Maniatis, T. (1989) Molecular Cloning, Second Edition, Cold Spring Harbor Laboratory Press, Plainview, N.Y.
9. Burgoyne, L. A., Carroll, D. J., Rogers, C. and Turner, J. (1997) Conventional DNA Collection and Processing: Disposable Toothbrushes and FTA® Paper as a Non-threating Buccal-Cell Collection Kit Compatible with Automatable DNA Processing. 8th International Symposium on Human Identification

What is claimed is:

1. A method of producing one or more cDNA molecules comprising:
   (a) contacting a sample comprising a cell or a virus with a solid medium, wherein:
      (i) the sample comprises mRNA and genomic DNA;
      (ii) the mRNA comprises an mRNA-template of interest; and
      (iii) wherein the solid medium comprises:
         a matrix; and
         a composition for inhibiting degradation of the mRNA template, wherein:
            the composition comprises a detergent or surfactant; and
            the composition is sorbed to the matrix then dried prior to contact with the sample;
   (b) sorbing at least a portion of the mRNA template to the solid medium;
   (c) eluting the mRNA from the solid medium while retaining the genomic DNA; and
   (d) contacting the mRNA with one or more reverse transcriptases under conditions sufficient to synthesize one or more cDNA molecules complementary to all or a portion of the mRNA template of interest.

2. The method of claim 1, wherein the cDNA is a cDNA library.

3. The method of claim 1, wherein the cDNA is double-stranded.

4. The method of claim 1, further comprising:
   (e) amplifying the cDNA.

5. The method of claim 4, wherein the amplifying step comprises contacting at least one cDNA strand with a polymerase under conditions to synthesize one or more cDNA molecules complementary to all or a portion of the template.

6. The method of claim 4, wherein the amplifying step comprises a polymerase chain reaction (PCR).

7. The method of claim 1, wherein the detergent or surfactant of the composition is an anionic detergent or surfactant and wherein the composition further comprises:
   (a) a base; and
   (b) a chelating agent.

8. The method of claim 7, wherein the composition further comprises uric acid or a urate salt.

9. The method of claim 7, wherein:
   (a) the anionic detergent or surfactant comprises sodium dodecyl sulfate (SDS);
   (b) the base comprises Tris or tris-hydroxymethyl methane; and
   (c) the chelating agent comprises ethylene diamine tetraacetic acid (EDTA).

10. The method of claim 1, wherein the matrix comprises a cellulose-based matrix or paper, or a micromesh of synthetic plastic material.

11. The method of claim 1, wherein the matrix is selected from the group consisting of nitrocellulose, cellulose, diazocellulose, carboxymethylcellulose, hydrophilic polymers, polytetra-fluoro-ethylene, fiberglass, porous ceramics, polystyrene, polyvinylchloride, polypropylene, polyethylene, dextran, agarose, agar, starch, and nylon.

12. The method of claim 1, wherein the sample comprises a eukaryotic cell.

13. The method of claim 1, wherein the eluting step further comprises contacting the solid medium comprising the mRNA with an elution buffer, wherein the elution buffer comprises:
   (a) a base;
   (b) a chelating agent;
   (c) dithiothreitol; and
   (d) a ribonuclease inhibitor.

14. The method of claim 13, wherein the elution buffer further comprises:
   (e) glycogen.

15. The method of claim 13, wherein:
(a) the base comprises Tris or tris-hydroxymethyl methane; and
(b) the chelating agent comprises ethylene diamine tetraacetic acid (EDTA).

16. The method of claim 13, wherein the eluting step further comprises incubating the solid medium comprising the mRNA with the elution buffer at a temperature at or below 4° C.

17. The method of claim 13, wherein the eluting step further comprises vortexing the solid medium comprising the mRNA with the elution buffer.

* * * * *

SEQUENCE LISTING

<160> NUMBER OF SEQ ID NOS: 14

<210> SEQ ID NO 1
<211> LENGTH: 22
<212> TYPE: DNA
<213> ORGANISM: Artificial sequence
<220> FEATURE:
<223> OTHER INFORMATION: Description of Artificial Sequence: Synthetic
      oligonucleotide

<400> SEQUENCE: 1
ctgcagtccc aggctattca gg                                                22

<210> SEQ ID NO 2
<211> LENGTH: 22
<212> TYPE: DNA
<213> ORGANISM: Artificial sequence
<220> FEATURE:
<223> OTHER INFORMATION: Description of Artificial Sequence: Synthetic
      oligonucleotide

<400> SEQUENCE: 2
agacttggac catgacggtg at                                                22

<210> SEQ ID NO 3
<211> LENGTH: 21
<212> TYPE: DNA
<213> ORGANISM: Artificial sequence
<220> FEATURE:
<223> OTHER INFORMATION: Description of Artificial Sequence: Synthetic
      oligonucleotide

<400> SEQUENCE: 3
ctgctgaaag agatgcggtg g                                                 21

<210> SEQ ID NO 4
<211> LENGTH: 21
<212> TYPE: DNA
<213> ORGANISM: Artificial sequence
<220> FEATURE:
<223> OTHER INFORMATION: Description of Artificial Sequence: Synthetic
      oligonucleotide

<400> SEQUENCE: 4
tcttcccaaa atgccctgag t                                                 21

<210> SEQ ID NO 5
<211> LENGTH: 23
<212> TYPE: DNA
<213> ORGANISM: Artificial sequence
<220> FEATURE:
<223> OTHER INFORMATION: Description of Artificial Sequence: Synthetic
      oligonucleotide

<400> SEQUENCE: 5
tcgccgatct gactaatgag gag                                               23

<210> SEQ ID NO 6
<211> LENGTH: 23
<212> TYPE: DNA
<213> ORGANISM: Artificial sequence
<220> FEATURE:
<223> OTHER INFORMATION: Description of Artificial Sequence: Synthetic
      oligonucleotide

<400> SEQUENCE: 6

```
atgcgcttca ttgccttcac tcc                                          23

<210> SEQ ID NO 7
<211> LENGTH: 22
<212> TYPE: DNA
<213> ORGANISM: Artificial sequence
<220> FEATURE:
<223> OTHER INFORMATION: Description of Artificial Sequence: Synthetic
      oligonucleotide

<400> SEQUENCE: 7
caagatgtgg aacagtggat tc                                           22

<210> SEQ ID NO 8
<211> LENGTH: 25
<212> TYPE: DNA
<213> ORGANISM: Artificial sequence
<220> FEATURE:
<223> OTHER INFORMATION: Description of Artificial Sequence: Synthetic
      oligonucleotide

<400> SEQUENCE: 8
catctatctt gatgttgtaa caagc                                        25

<210> SEQ ID NO 9
<211> LENGTH: 18
<212> TYPE: DNA
<213> ORGANISM: Artificial sequence
<220> FEATURE:
<223> OTHER INFORMATION: Description of Artificial Sequence: Synthetic
      oligonucleotide

<400> SEQUENCE: 9
cctcgccttt gccgatcc                                                18

<210> SEQ ID NO 10
<211> LENGTH: 23
<212> TYPE: DNA
<213> ORGANISM: Artificial sequence
<220> FEATURE:
<223> OTHER INFORMATION: Description of Artificial Sequence: Synthetic
      oligonucleotide

<400> SEQUENCE: 10
ggatcttcat gaggtagtca gtc                                          23

<210> SEQ ID NO 11
<211> LENGTH: 23
<212> TYPE: DNA
<213> ORGANISM: Artificial sequence
<220> FEATURE:
<223> OTHER INFORMATION: Description of Artificial Sequence: Synthetic
      oligonucleotide

<400> SEQUENCE: 11
cccagtgaca ggaggagacc ata                                          23

<210> SEQ ID NO 12
<211> LENGTH: 23
<212> TYPE: DNA
<213> ORGANISM: Artificial sequence
<220> FEATURE:
<223> OTHER INFORMATION: Description of Artificial Sequence: Synthetic
      oligonucleotide

<400> SEQUENCE: 12
```

-continued

```
atcctgtgct ttttctgtgg gac                                    23

<210> SEQ ID NO 13
<211> LENGTH: 54
<212> TYPE: DNA
<213> ORGANISM: Artificial sequence
<220> FEATURE:
<223> OTHER INFORMATION: Description of Artificial Sequence: Synthetic
      oligonucleotide

<400> SEQUENCE: 13
gactagttct agatcgcgag cggccgccct tttttttttt tttttttttt tttt     54

<210> SEQ ID NO 14
<211> LENGTH: 44
<212> TYPE: DNA
<213> ORGANISM: Artificial Sequence
<220> FEATURE:
<223> OTHER INFORMATION: Description of Artificial Sequence: Synthetic
      primer-adapter oligonucleotide
<220> FEATURE:
<223> OTHER INFORMATION: biotinylated sequence

<400> SEQUENCE: 14
gactagttct agatcgcgag cggccgccct tttttttttt tttt               44
```